United States Patent [19]
Kun et al.

[11] Patent Number: 5,807,272
[45] Date of Patent: Sep. 15, 1998

[54] IMPEDANCE SPECTROSCOPY SYSTEM FOR ISCHEMIA MONITORING AND DETECTION

[75] Inventors: Steven Kun, Worcester; Robert A. Peura, Princeton; Borislav Ristic, Worcester, all of Mass.

[73] Assignee: Worcester Polytechnic Institute, Worcester, Mass.

[21] Appl. No.: 739,162

[22] Filed: Oct. 30, 1996

[51] Int. Cl.[6] ........................................ A61B 5/04
[52] U.S. Cl. ............................................ 600/547
[58] Field of Search ................... 600/481, 486, 600/500, 504, 506, 547, 528, 546

[56] References Cited

U.S. PATENT DOCUMENTS 5,280,429  1/1994  Withers ........................... 364/413.25
5,282,480  2/1994  Hudrlik ................................... 607/28

OTHER PUBLICATIONS

Gebhard, M.M., "Impedance Spectroscopy: A Method for Surveillance of Ischemia Tolerance of the Heart," *Thorac Cardiovasc. Surgeon* 35, pp. 26–32 (1987).

Primary Examiner—Francis Jaworski
Attorney, Agent, or Firm—Hamilton, Brook, Smith and Reynolds, P.C.

[57] ABSTRACT

An impedance spectroscopy tissue status monitoring and measurement system is disclosed. The system uses a synthesizer to generates electrical signals of selected frequencies. An electrical current source is responsive to the synthesizer and generates electrical currents for transmission through tissue. Electrodes or inductive coils of the system apply the electrical current to the tissue and sense voltages generated in the tissue in response to the electrical current. A controller determines the spectral response of the tissue by detecting magnitude and phase information of the electrical energy transmitted through the tissue. The information is then used to determine volumes of compartments within the tissue and ionic concentrations of compartmental fluids. Capacitive effects derived from the phase information are used to determine cell membrane functionality within the tissue. From this analysis, status, specifically, ischemia, may be determined on an absolute basis.

31 Claims, 15 Drawing Sheets

CALCULATE SIGNAL PARAMETERS

(Using both actual data and modeled data generated by extrapolation of the best fit impedance locus)

- Low frequency resistivity plateau RHOO
- Dispersion slope REDS
- Width of dispersion region REDW
- Maximum phase angle freq. FPHMAX
- Positive slope of the phase PHPS
- Width of phase positive slope PHPSW
- Maximum reactance freq. FIMMAX
- Positive slope of reactance IMPS
- Width of reactance positive slope IMPSW
- TAU of the complex impedance locus
- High frequency resistivity plateau RHO ∞
- Central dispersion frequency FRECD
- Maximum phase angle PHMAX
- Negative slope of the phase PHNS
- Width of the negative slope of phase PHNSW
- Maximum of absolute reactance IMMAX
- Negative slope of the reactance IMNS
- Width of reactance negative slope IMNSW
- ALPHA of the complex impedance locus
- IMSR = IMPS/IMNS, etc.

520

CALCULATE THE ANGLES BETWEEN THE ELECTRODES AND THE LONGITUDINAL MUSCLE AXIS

Use a pattern recognition scheme, based on a numerical mathematical model of the current distribution in the specific sample

525

FIG. 5B

IMPEDANCE SPECTROSCOPY SYSTEM FOR ISCHEMIA MONITORING AND DETECTION

RELATED APPLICATIONS

This application claims priority to U.S. Provisional Application No. 60/008,148, filed Oct. 31, 1995, the contents of which is incorporated herein by reference in its entirety.

BACKGROUND OF THE INVENTION

Assessment of tissue perfusion/ischemia is of critical importance in a number of medical applications. In plastic and reconstructive surgery it is used for postoperative monitoring of transplanted muscle flaps. A prerequisite for a successful operation and outcome is proper perfusion or passage of blood through the vascular bed of the transplanted tissue. It is essential to know as early as possible after surgery if the tissue is becoming ischemic, i.e., locally anemic due to some mechanical obstruction or other reason, and thus jeopardized. In this event, rapid surgical intervention can be used for corrective measures. A very similar application exists in cardiology where myocardium ischemia monitoring is of crucial importance. Also, measurement of ischemia in the legs due to arteriosclerotic plaque (or other reasons) is a problematic area. Monitoring and measuring ischemia levels during long "blood-less" reconstructive surgeries of arms and legs, where the blood perfusion is intentionally stopped to enable delicate surgery without significant blood loss, is of significant importance as an indicator of the patient's well being.

There are numerous methods for monitoring muscular perfusion. Techniques that image the vasculature directly include: Doppler, duplex scanning, angioscopy, and arteriography. Indirect methods include: pH measurements, transcutaneous $PO_2$ monitoring, laser Doppler, and fluorescein staining.

Each of these techniques, however, has its attendant drawbacks. Doppler monitoring and duplex scanning operate by detecting the flow of blood though the tissue or arteries in question. The equipment tends to be expensive and requires a doctor or other technician to interpret the results. In fluorescein staining, a chemical is administered to the patent. The patient's skin is then exposed to ultraviolet light, and perfused sections of the skin will exhibit fluorescence from the staining. The administration of the chemical, however, is undesirable. Moreover, the chemical has a limited half-life in the body. This limits this technique to one-time detection.

The most commonly used of the techniques is pH monitoring. When tissue is not adequately perfused, and it becomes ischemic, the acidity increases due to the accumulation of metabolic products. Therefore, by measuring the pH, predictions can be made as to how well the tissue is perfused. Unfortunately, pH can only be detected with at least one active electrode implanted in the tissue, which is invasive and suffers from long term measurement instability.

Attempts have been made to use impedance spectroscopy to detect stress imposed on the tissue by interruptions in perfusion or hyperthermia, for example. The work in this area has been directed to extracting information that will be characteristic of the changes induced in the tissue by the stress. One useful mechanism has been the Cole-Cole dispersion plot of tissue reactance as a function of resistance for various frequencies. The work in this area has been successful in monitoring changes in the tissue's electrical properties using the spectroscopy techniques.

The problem with these known impedance spectroscopy techniques, however, is their general inability to detect ischemia on an absolute basis. Much of the work deals with situations in which the blood supply to the tissue is occluded or the tissue is exposed to heat. The techniques monitor the effects of these stresses on the tissue over time. While interesting from a research standpoint, these techniques have little clinical value. What is needed is the ability to measure the level of ischemia even when a precise knowledge of the tissue's initial condition is unknown.

SUMMARY OF THE INVENTION

The present invention is directed to a tissue status monitoring and measurement system that is based on the principles of impedance spectroscopy. Consequently, the approach is non- or minimally-invasive, harmless to the patient, appropriate for long term monitoring, provides single quantitative results, and the necessary instrumentation is simple to use for medical personnel and relatively inexpensive.

In general, according to one aspect, the invention features a method for the detection of tissue ischemia. The method comprises applying electrical energy to the tissue that is to be analyzed. The spectral response of the tissue to the energy is then detected. The information gained from the response is then transformed into a measure of the ischemia of the tissue.

In specific embodiments, the step of applying electrical energy comprises generating sinusoidal currents of varying frequencies in the tissue. The frequencies can range between approximately 10 Hertz(Hz) and 1 MHZ.

In other aspects of the embodiments, the transformation step includes modeling the spectral response of the tissue when normal based upon the detected spectral response. This may be accomplished by extrapolating a resistance/reactance relationship into higher frequencies based upon a resistance/reactance relationship at lower frequencies. The detected spectral response of the tissue is then compared to the modeled spectral response to determine the measure of the ischemia.

In the preferred embodiment, the transformation is completed using a pattern matching algorithm that is trained to generate the measure of ischemia. The algorithm typically necessitates the generation of parameters that are descriptors of a spectral response of the ischemia of the tissue based upon the detected spectral response—in addition to—the generation of parameters that are descriptors of the spectral response of the tissue when normal based upon the extrapolated high frequency response. The two types of parameters are then compared for patterns that are indicative of a certain level of ischemia.

In order to assist in the accuracy of the system, resistive and/or capacitive components of an electrical model of the tissue may be computed and used to preprocess the parameters prior to input into the pattern matching algorithm.

The invention, however, is not limited to only detecting ischemia as it may be used to generally detect a status of tissue. The status may, for example, include whether or not tissue contains abnormal cells or tumor cells, is hypoxic, or is damaged. In this case, the invention again includes a spectral response detection with the addition of combining parameters derived from the detected spectral response of the tissue in a pattern matching algorithm that is trained to generate a measure of the status. Here again, the disclosed normal tissue modeling techniques are helpful.

In general according to another aspect, the invention also features a system for the detection of tissue ischemia or status generally. The system uses a synthesizer to generate electrical signals. An electrical current source is responsive to the synthesizer and generates electrical currents for transmission through tissue in response to the electrical signals. Some means are then used to insert the electrical current into the tissue and sense voltages generated in the tissue in response to the electrical current. This may include electrodes, coils, other energy radiators, or other techniques that allow the spectral response detection. A controller then executes a pattern matching algorithm that is trained to generate a measure of the tissue's status in response to parameters derived from a spectral response of the tissue.

In embodiments, the system may further include an analog-to-digital converter for digitizing the sensed voltages for the controller and a synchronization circuit for coordinating the operation of the synthesizer and the analog-to-digital converter. A bandpass filter is also helpful for filtering the sensed voltages prior to digitization by the analog to digital converter.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

1. Electrical Behavior of Tissue

By way of background, biological tissues, such as skeletal muscle, exhibit complex electrical responses. Skeletal muscle tissue is electrically anisotropic: its resistivity is lower along the longitudinal axis of the cell than across it. Moreover, it is presently accepted that tissues can be described with a so-called bi-domain model. The first domain is the extracellular space and the second domain is the intracellular space, each having different associated resistances. The two domains are separated by the cell membrane that provides a capacitive effect.

Figure 1:
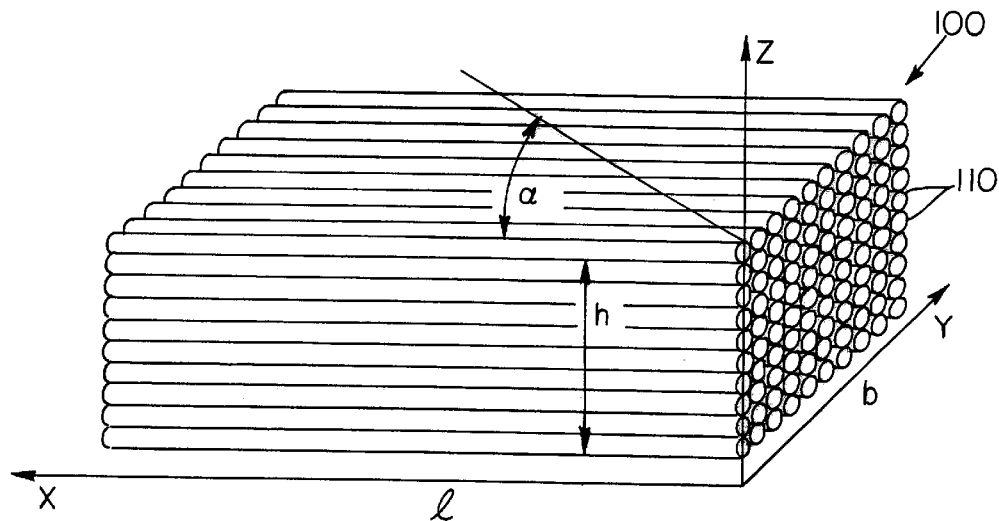
FIG. 1 is a simplified representation of a skeletal muscle slab in which the cells appear as closely packed pipes.

FIG. 1 shows a simplified representation of a skeletal muscle slab 100 placed in a rectangular coordinant system in which the X-Y plane is parallel to the skin. The skeletal muscle cells 110 appear as closely packed pipes, each individual cylinder or pipe representing a single skeletal muscle cell. l is the length, h is the height, and b is the width of the muscle slab 100. The angle (a) is the angle between an electrode assembly axis and the longitudinal axis (x) of the muscle cells 110.

Figure 2:
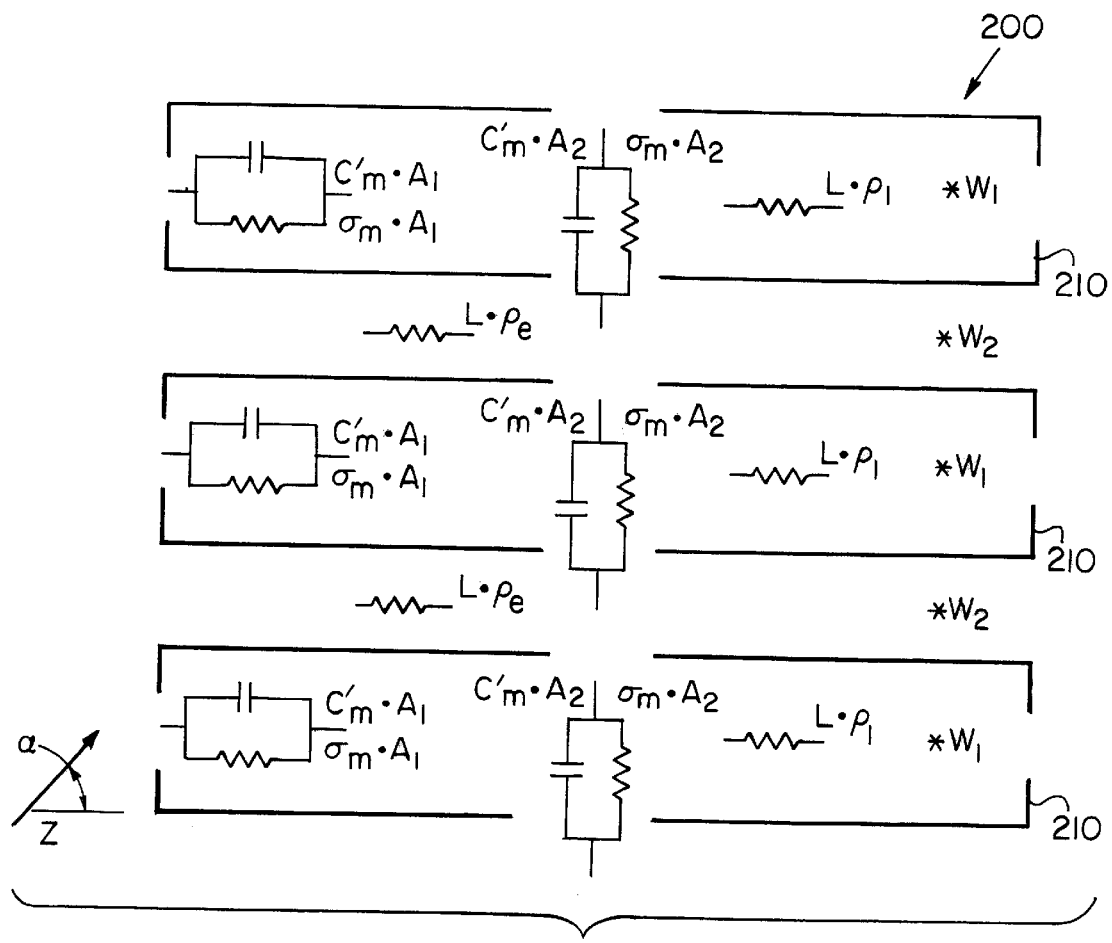
FIG. 2 is an electrical model of a muscle cell bundle.

FIG. 2 shows an electrical model 200 of a muscle cell bundle. Each rectangular region 210 represents a muscle cell with L being the cell length, $W_1$ and $W_2$ are the weighting factors of the intra- and extra-cellular space, respectively, $\rho_i$ and $\rho_e$ (RHO) are the resistivities of the intra-and extracellular spaces. $C_m$ and $\sigma_m$ are the capacitance and conductivity of the cell membrane. $A_1$ and $A_2$ are the surface areas of the base and lateral surfaces, respectively, of the cell cylinder.

2. Impedance Spectroscopy System Hardware

Figure 3:
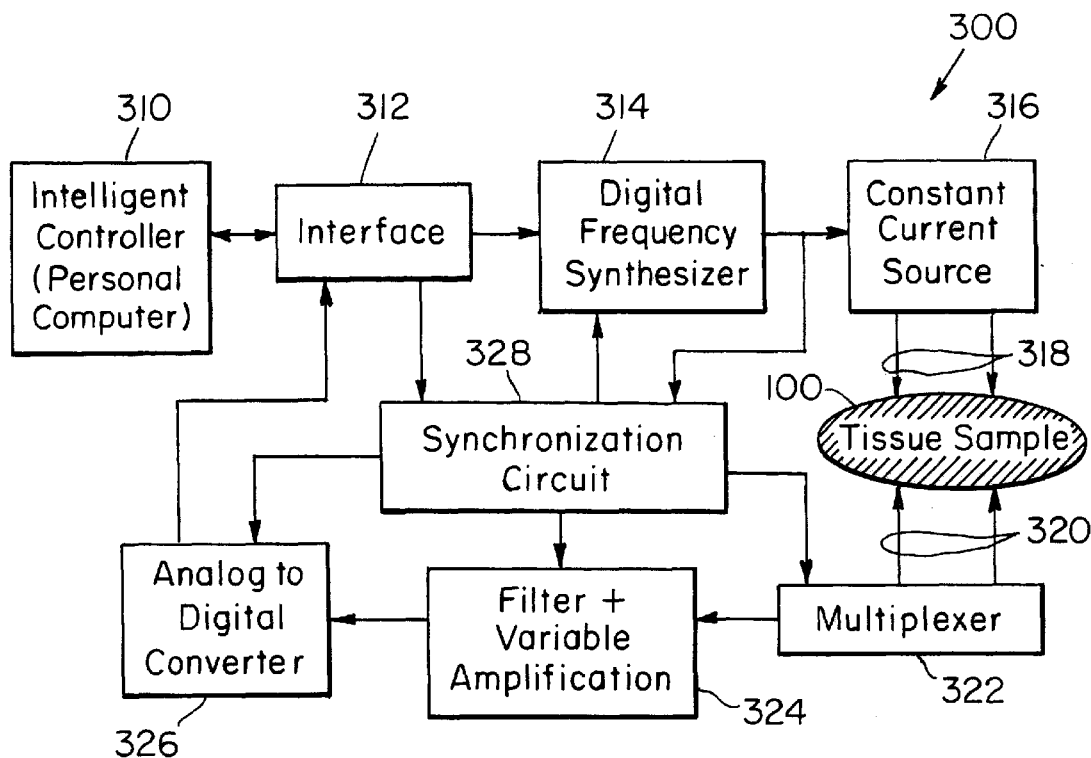
FIG. 3 shows an inventive impedance spectroscopy system for perfusion/ischemia level monitoring and measurement.

FIG. 3 shows an impedance spectroscopy system 300 that has been constructed according to the principles of the present invention. Generally, an intelligent controller 310, such as a personal computer or microcontroller, interfaces with the environment via an interface module 312. The module 312 connects to a digital frequency synthesizer 314 that produces a sine wave voltage signal of a frequency and amplitude selected by the controller 310 via the interface module 312. A constant current source 316 controls an amplitude of the sinusoid current generated by the synthesizer for injection into the tissues 100 via source electrodes 318.

Figure 4:
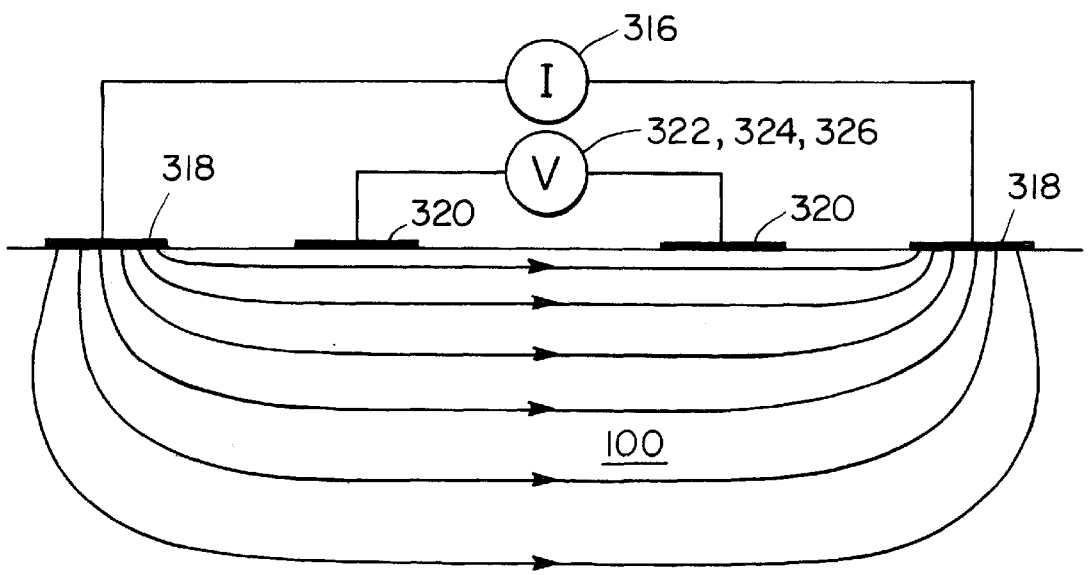
FIG. 4 illustrates a preferred electrode configuration for attaching the system to a patient.

FIG. 4 illustrates the preferred electrode configuration. Two outer source surface-spot electrodes 318 connect the constant current source 316 to the tissue 100, e.g., muscle slab. The inner detection electrodes 320 in one implementation are then used to monitor the resulting voltage at the tissue 100. For some applications, however, more accurate results may be obtained from needle-type electrodes, especially where the targeted tissue is located below more superficial muscle layers, dermal layers, and fat.

Non-contact solutions may be desired for other embodiments. The electrical current can be generated in the tissue inductively. A coil is located above the tissue and the desired electrical current induced by generated magnetic fields. Measurements are made by determining the tissue impedance that is coupled into the coil. Generally, any technique that will enable the generation of the required electrical fields within the tissue is acceptable.

Returning to FIG. 3, a multiplexer 322 is connected to the detection electrodes 320. This component is required to select the input to the measurement portion of the circuit. It provides selection among the available tissue voltage electrode sets if multiple sets are available, current measurement resistors, and system calibration resistors.

An amplifier/filter 324 receives the selected output from the multiplexer 322. It has a software controlled variable gain with filtering capabilities. Specifically, band-pass filtering is performed for anti-aliasing and noise reduction. The cut-off frequencies of the filter are also software selectable.

An analog-to-digital converter 326 provides the digitized data to the controller 310. Synchronization circuitry 328 is required to find accurate instances for in-phase and quadrature sampling.

3. Impedance Spectroscopy Ischemia Determination

Figure 5A:
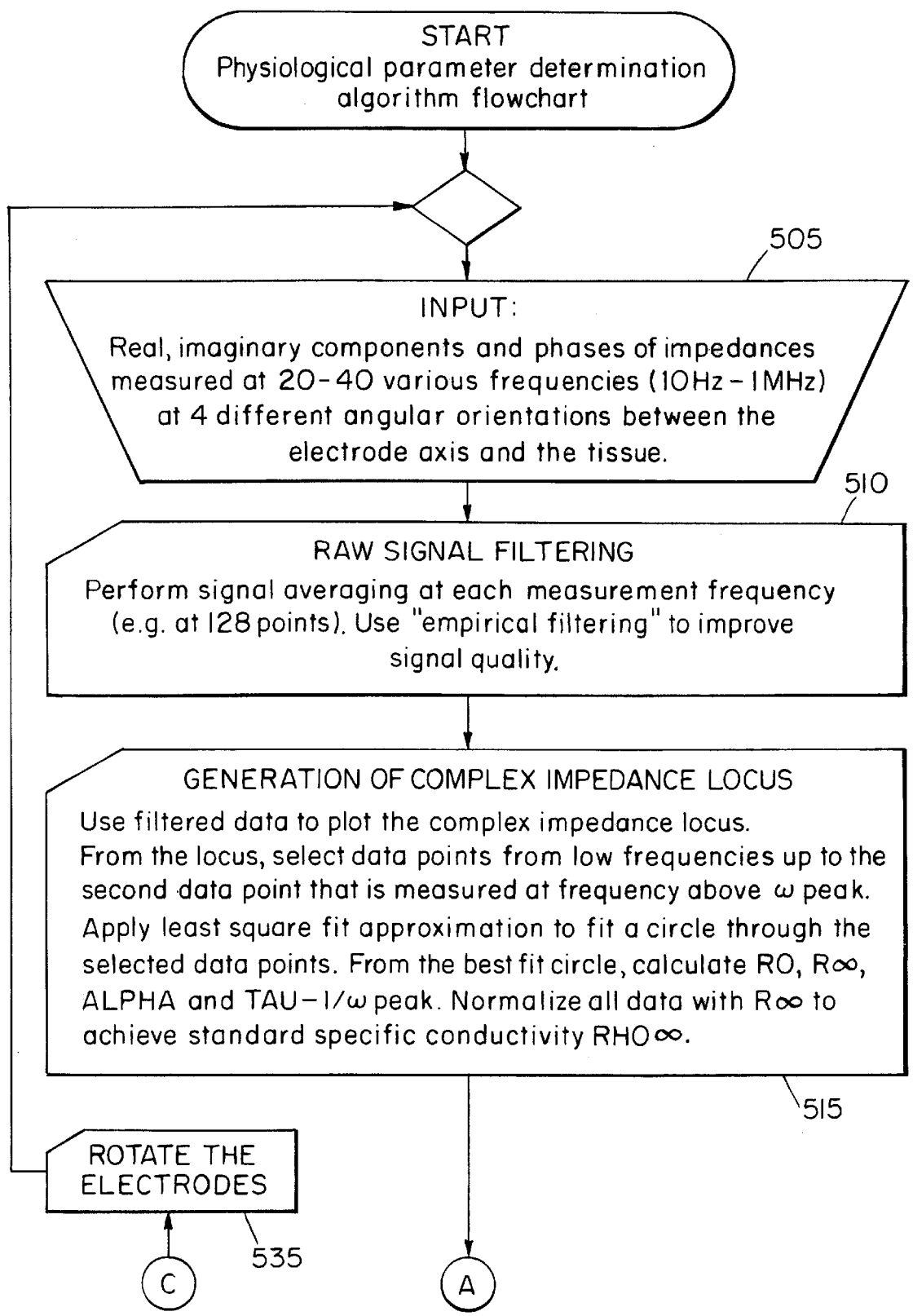
FIGS. 5A and 5B are a process diagram showing the operation of the inventive system for tissue perfusion/ischemia level monitoring and measurement.
Figure 5C:
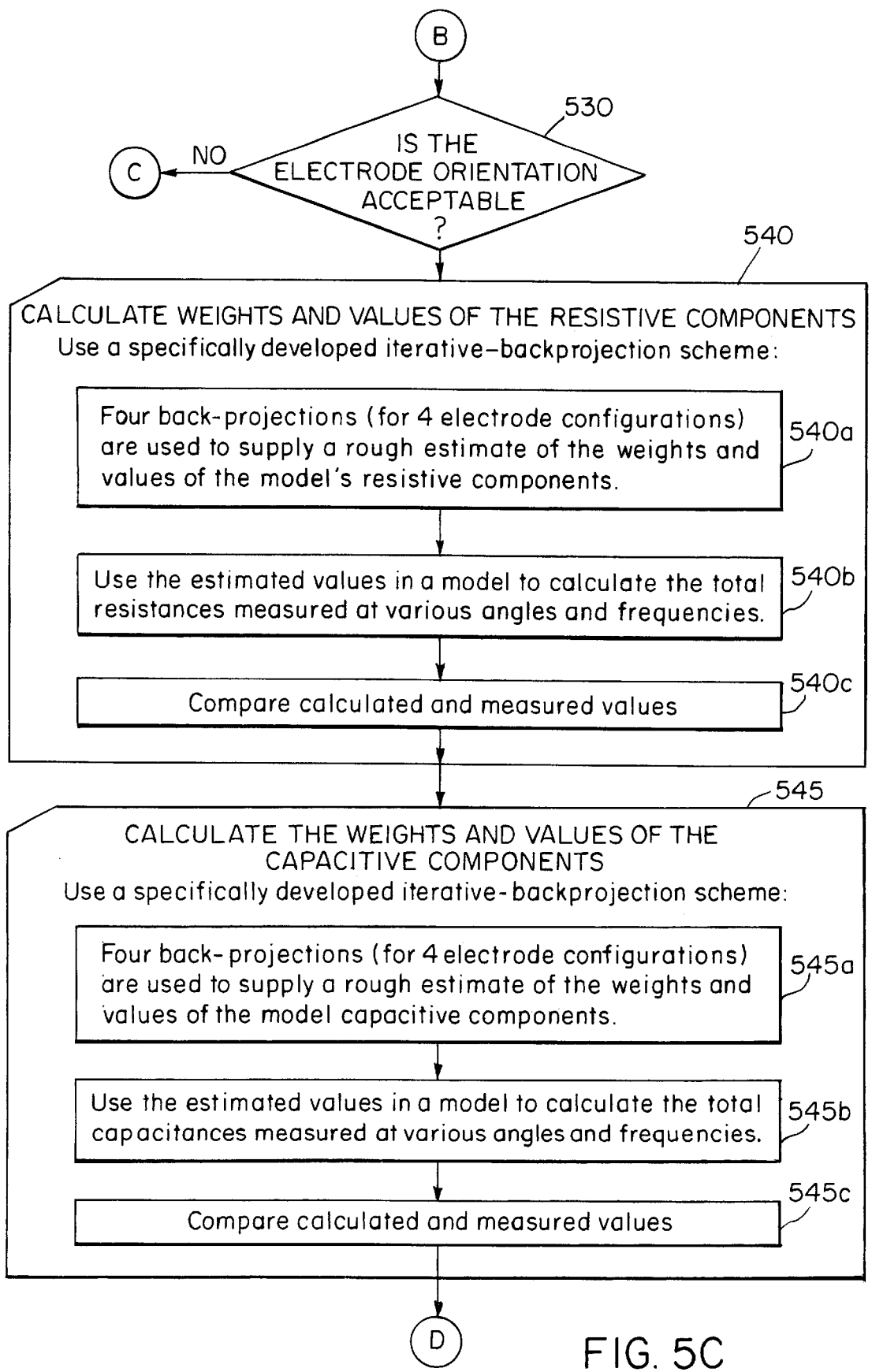
Figure 5D:
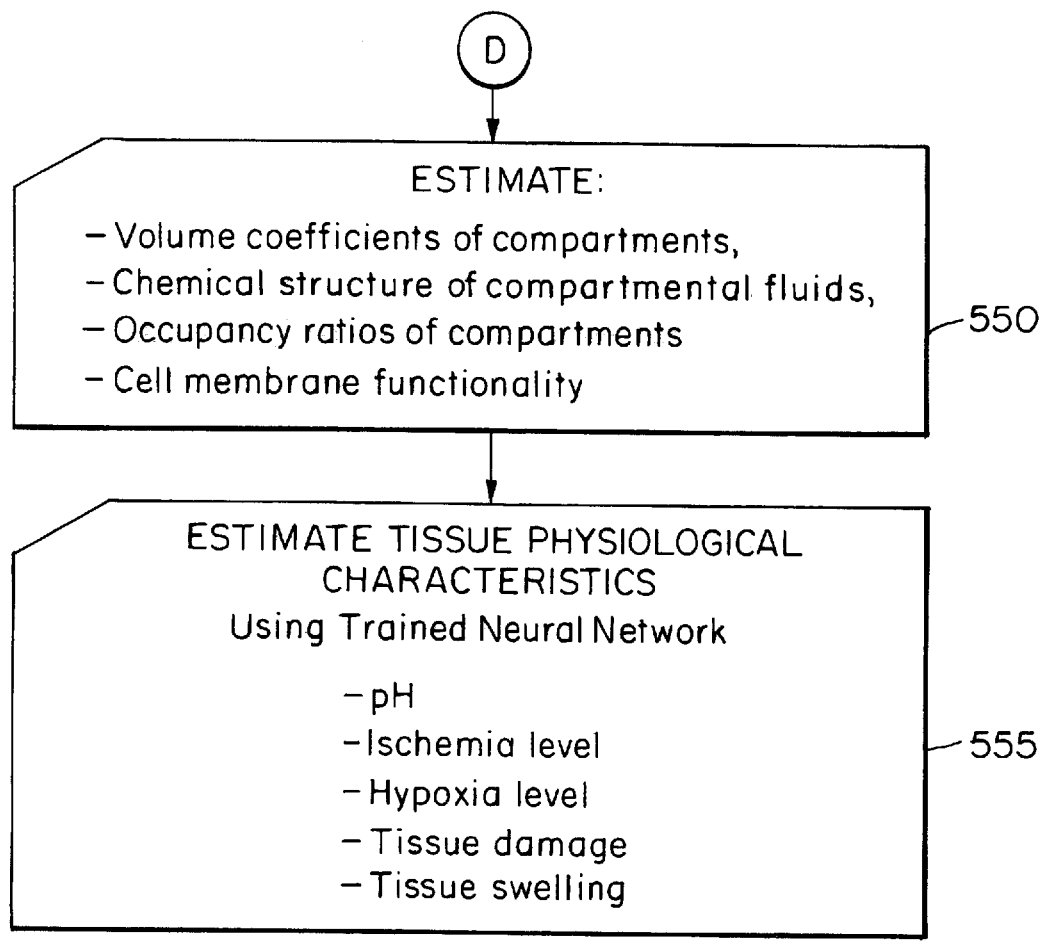

FIGS. 5A and 5B are process diagrams illustrating the data acquisition, signal processing, and transform performed by the hardware system, and principally the controller 310, to estimate the physiological characteristics or status of the tissues 100 based upon its spectral response.

In step 505, the spectroscopy system 100 makes measurements of the resistance, reactance, and phase at multiple, such as 20–30, frequencies in the range of 10 Hz –1 MHZ. At each selected frequency, the digital frequency synthesizer 314 generates the sinusoid at the desired frequency and the constant current source 316 drives the current through the tissue sample 100 via the electrodes 318. Simultaneously, the analog-to-digital converter 326 samples the generated voltage via electrodes 320. Knowing the frequency, amplitude, and phase of the injected current, the impedance magnitude, and phase of the tissue are measured, and the resistance and reactance are calculated.

Principally, measurements are made along the longitudinal axis of the fibers, when the tissue 100 is a muscle slab. Measurements, however, are also preferably taken from multiple, such as four different, angular orientations of the electrodes 318, 320 relative to the tissue. Information from the different electrode orientations may be gained either by using multiple electrodes at different orientations or by moving the electrodes and remeasuring.

Prefiltering of the raw signal data is then performed in step 510. Low pass filtering by time averaging is preferably performed to remove any glitches that appear in the data. Additionally, it may be necessary to sometimes perform empirical filtering to improve signal quality. In this filtering step, signal patterns, appearing in the frequency domain, that can not be caused by physiological sources are removed. Such filtering may be necessitated by gain mismatching in the spectroscopy system 100 between the different stages for different frequencies.

Figure 6:
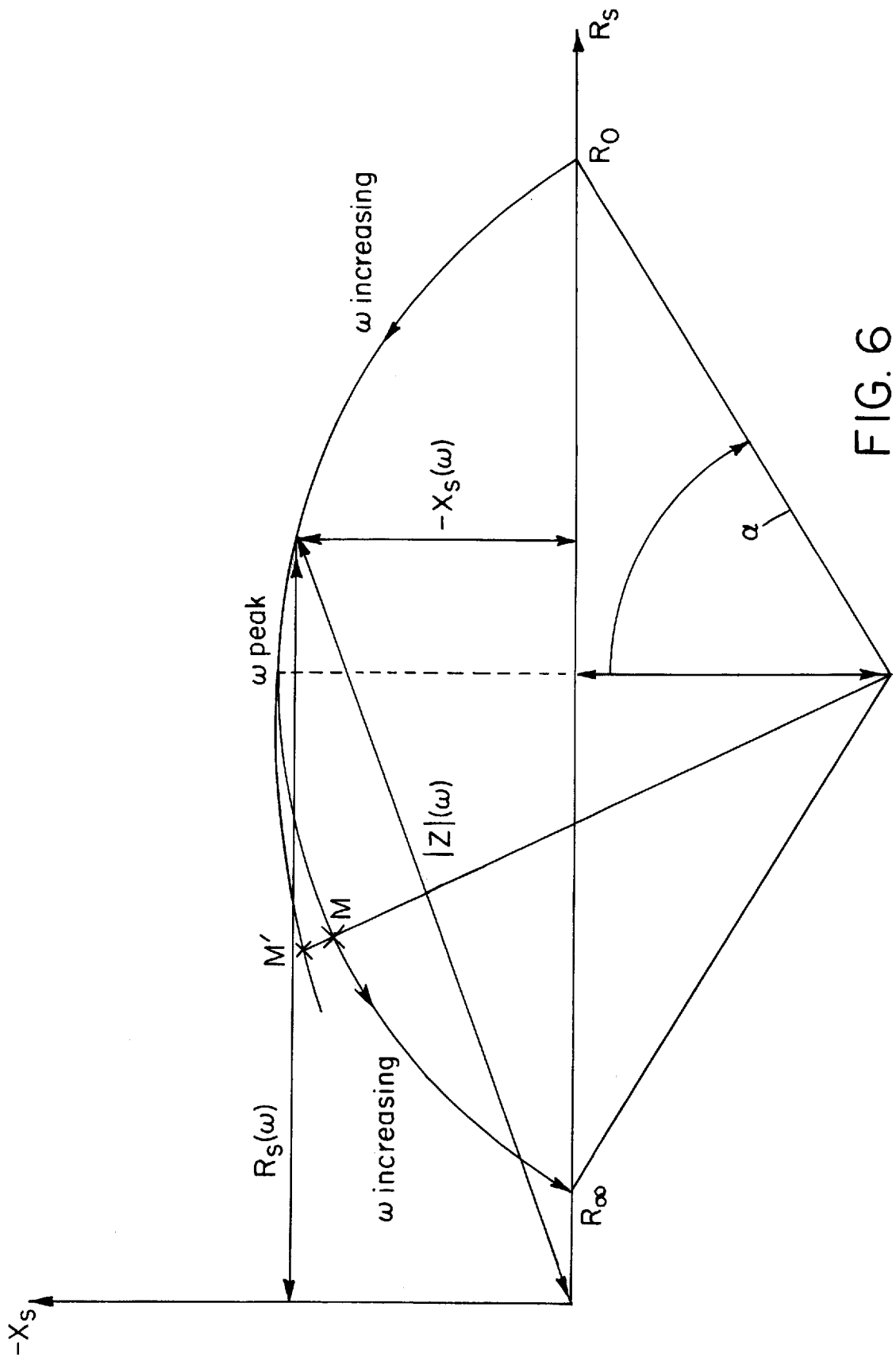
FIG. 6 is a Cole-Cole plot of the reactance as a function of resistance showing the depressed minor arch of a circle that lies below the real axis, which is characteristic of tissue impedance measurements.

In step 515, the acquired impedance data is converted into resistance and reactance space to generate a complex impedance locus in the Cole-Cole dispersion representation to find the tissue's physiological characteristics at the point in time. FIG. 6 illustrates an example of this representation. Data from a given acquisition from the subject tissue is plotted as the reactance ($-X_S$) as a function of the real component of the impedance (Z) or the resistance ($R_S$) for the various measured frequencies.

Our research has established that the interpretation of information contained in the Cole-Cole plot and its extrapolation can be used as a predictor or detector of an abnormal status of the tissue. Preferably, they are used to detect ischemia, but are also applicable to detecting tumor cells, hypoxia, damage, or swelling. Each cell, if it could be measured, would have its own frequency locus characteristics. The locus that is generated through impedance spectroscopy represents the net or average locus of the cells contributing to the detected tissue response.

Changes in the tissue's status can manifest in changes in the frequency locus plot. Generally, the right side of the locus semicircle, i.e., the portion to the right of ω peak, $\omega=2\pi f$, tends to be less directly useful in measuring ischemia on an absolute basis. It tends to be very sensitive to the particular type of muscle and the orientation of the electrodes relative to the muscle. As a result, it is generally a poor measure of tissue abnormal states.

The lower frequency reactance and resistance measurements, however, are useful in determining the frequency locus plot for the healthy or normal cell within the population of cells in the monitored tissue. The healthy cell will have a locus plot that is a smooth semicircle extending from $R_0$ to $R_\infty$. Ischemia, for example, tends to manifest itself in the frequency locus plot in the deviation between the ideal semicircle for the healthy cell and the divergence with increasing ω. This is represented in FIG. 6 by the difference between the ideal semicircle on which M is located and the deviation found in ischemic cells illustrated by the curve on which M' is located. This deviation between the M (ideal or normal cell curve) and M' curve represents changes in detected tissue reactance that are consequences of the breakdown of cellular membranes. With the onset of ischemia, the cell membrane's function is altered. This is enhanced by the increase in soluble metabolic byproducts that are not removed by circulating blood. Similar functional changes are present in tumor cells, hypoxic tissues, and tissues subject to swelling.

The objective of the signal processing is to use the frequency locus representation of the tissue's response to generate a second set of data points in addition to the actual detected spectral response. The first set of data points represents the reactance and resistance measured or detected from the tissue. This is the actual or real data. The second set of data is a modeled set of data that is used as a predictor of what the response of the tissue would be if it were healthy, non-ischemic, or otherwise normal. This modeled data is generated by extrapolating the semicircle using least square fit approximation based upon the data points of low angular frequencies omega (ω) and extrapolating these data into a continuous curve extending in the direction of the increasing omega (ω), or in the direction of $R_\infty$. Specifically, data points for low frequencies up to the second data point beyond omega (ω) peak are used to extrapolate the curve into the higher frequencies.

Figure 7:
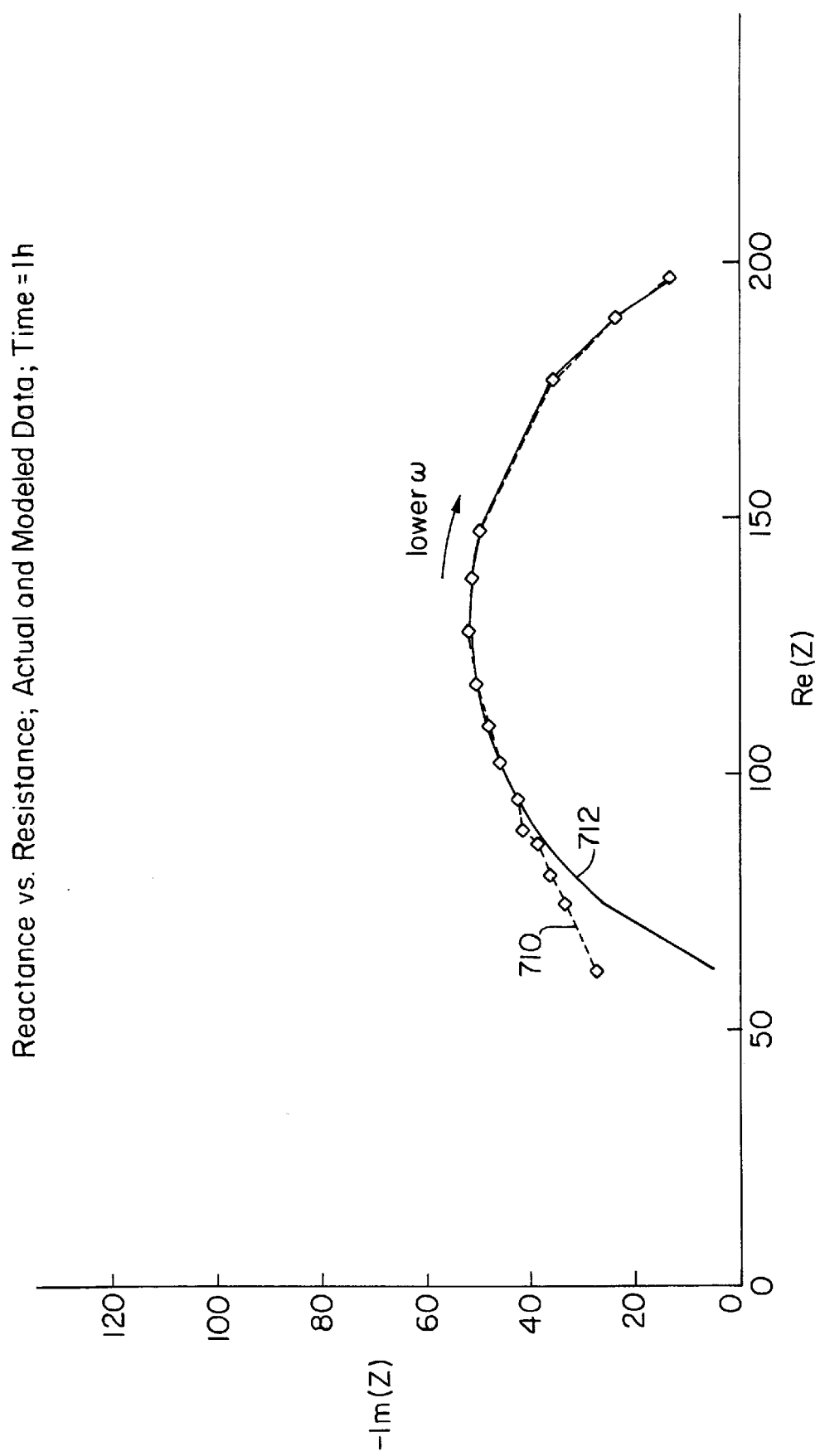
FIG. 7 is a Cole-Cole plot of actual impedance measurements from tissue and an extrapolation of the data based upon the low frequency data points.

FIG. 7 is a frequency locus plot of actual measured data taken from an ischemic muscle slab. The dotted line 710 and the data points (♦) represent actual measured reactance versus resistance values. The data points at the lower angular frequencies (ω) are used to create the modeled data by extrapolating the semicircle into the higher frequencies. This is represented by the solid line 712. It is the divergence between the modeled data 712 and the actual data 710 that is a predictor of ischemia. Ischemia is evidenced by the elevated magnitude of the reactance at higher omega (ω) or frequency data points.

Returning to FIG. 6, the modeled data based upon the best fit circle least square approximation, which is generated based upon the low omega (ω) data points, is used to calculate $R_0$, $R_\infty$ (which is highly correlated to the resistivity of the tissue since as ω approaches ∞, the contribution of the reactance to the impedance approaches 0), α, and τ=1/ω peak. Based upon known biochemical characteristics of living tissues, for example, electrolytic conductivity of human skeletal muscle is RHO∞=1.1 Ω-m, all measured and modeled resistances and reactances are normalized to specific resistances and specific reactances.

Figure 8:
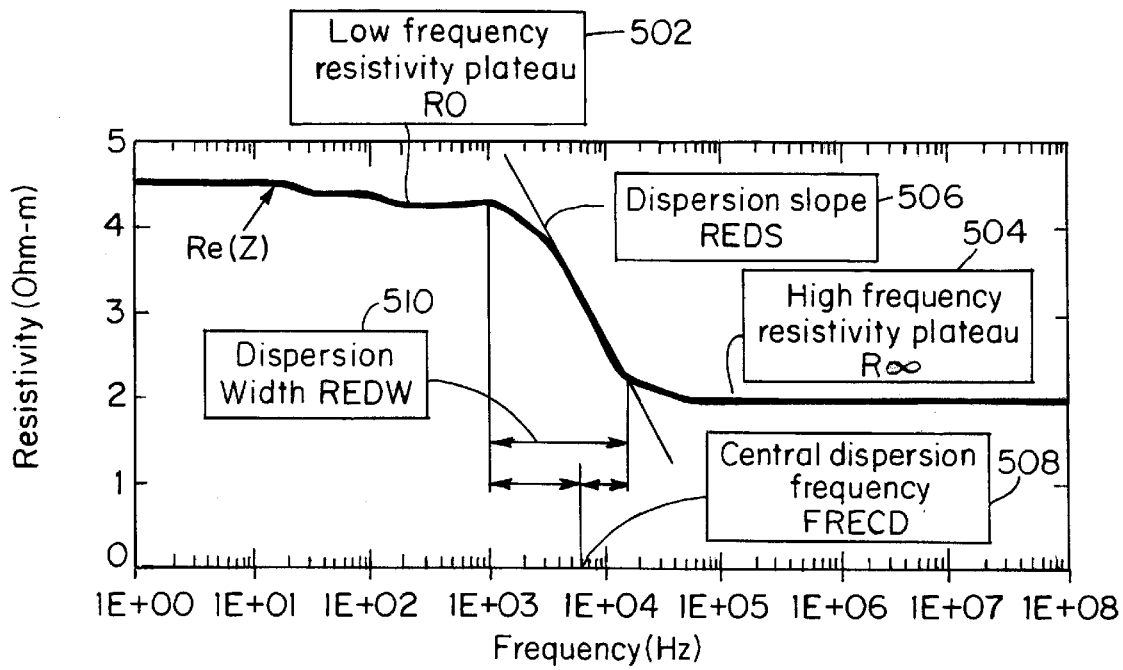
FIG. 8 is a plot of tissue resistivity as a function of frequency showing the parameters used by the system to detect perfusion/ischemia levels.
Figure 9:
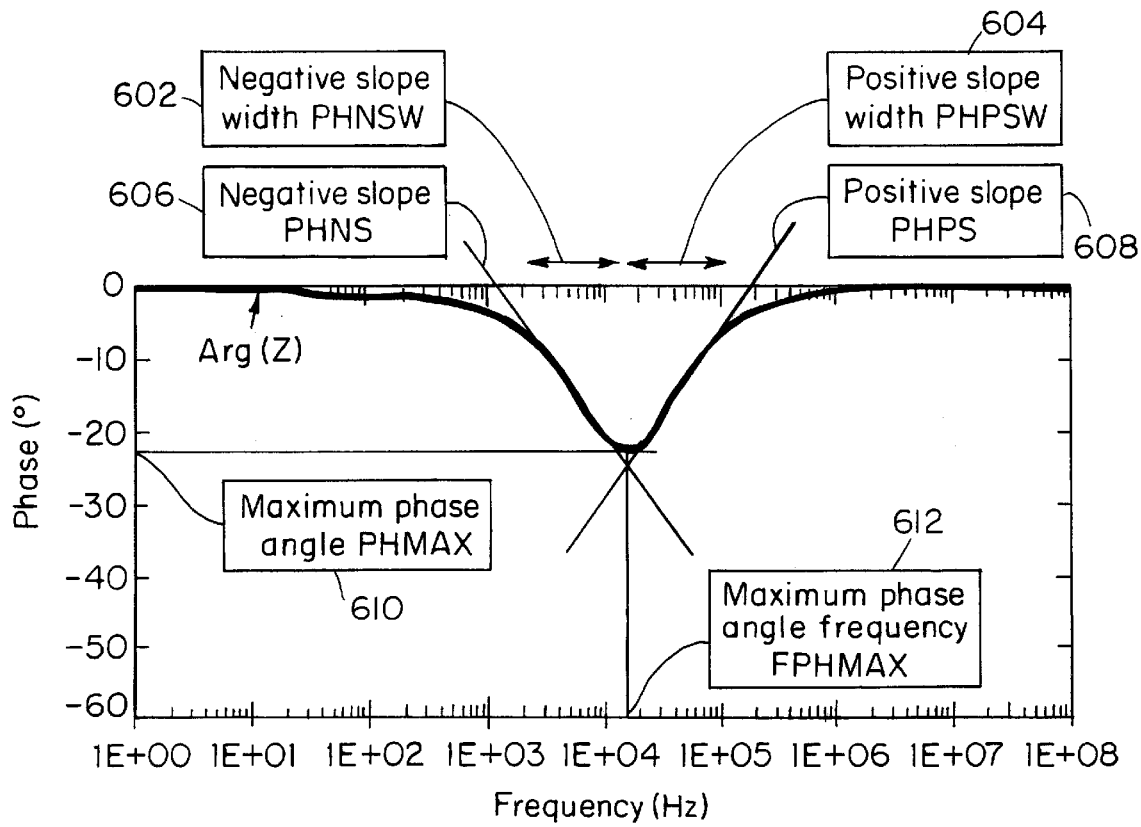
FIG. 9 is a plot of the tissue impedance phase as a function of frequency showing other parameters.
Figure 10:
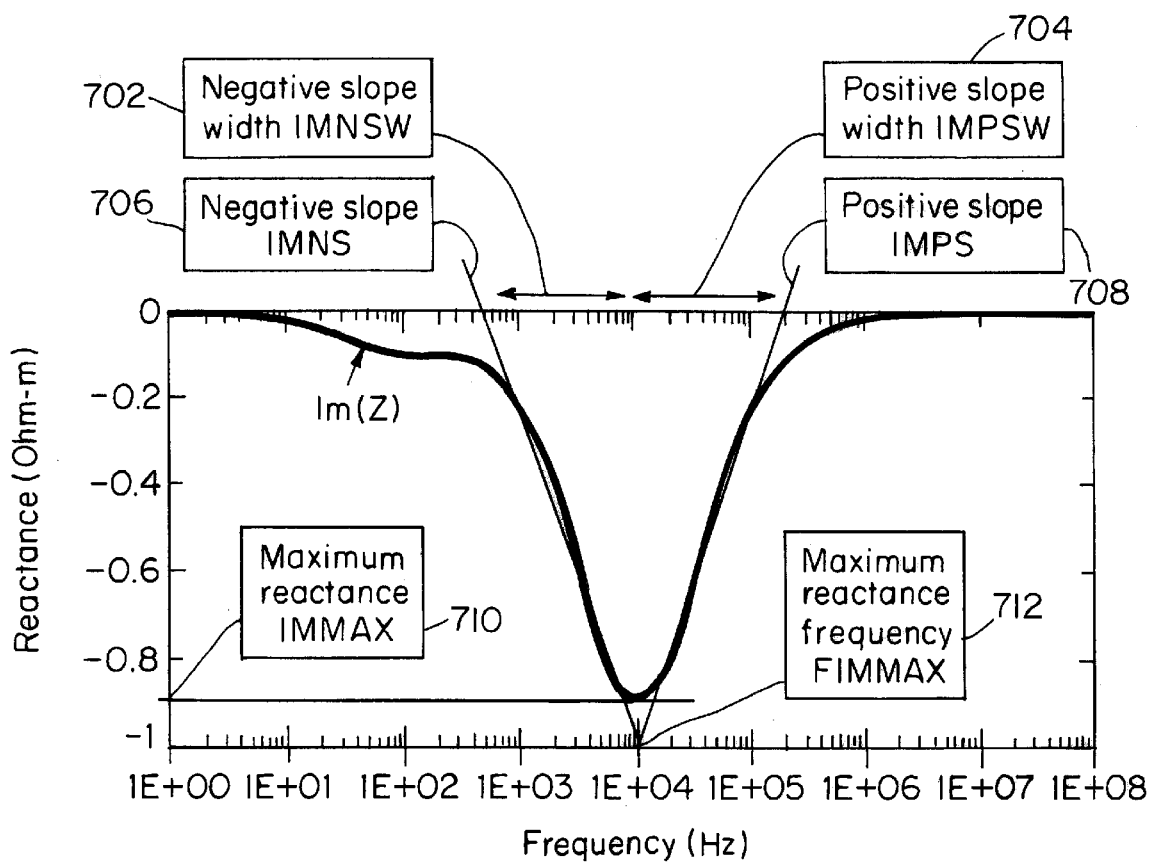
FIG. 10 is a plot of tissue reactance as a function of frequency showing still other parameters.
Figure 15:
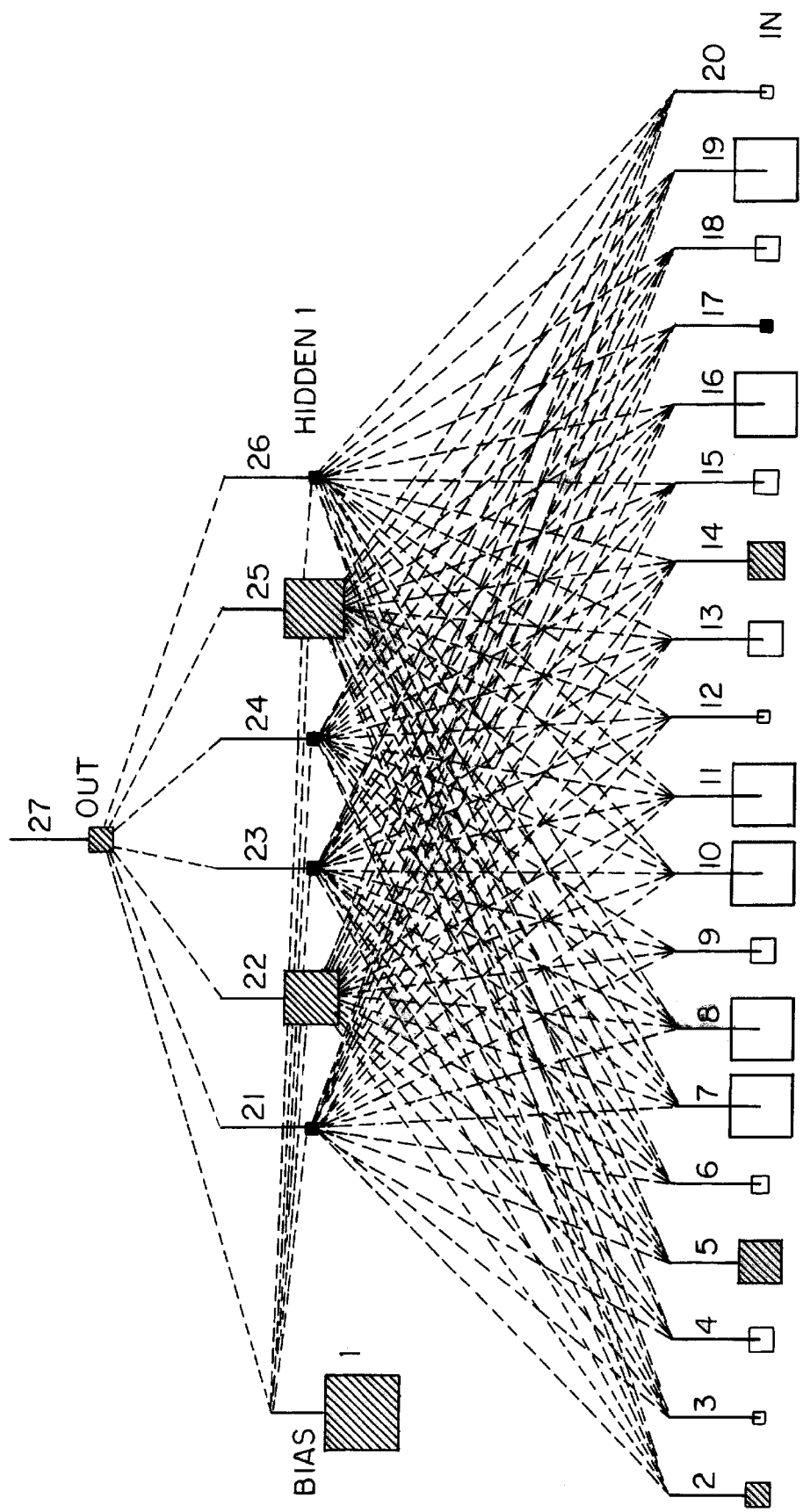
FIG. 15 shows the input parameters and the output for a trained neural network pattern matching algorithm.

In step 520, a series of parameters are extracted from the actual or real data points and the modeled data. Most will be later directly used by a pattern matching algorithm. In more detail, for a set of measurements or time interval each of the actual data points and the modeled data points are plotted as resistivity (Ohm-m) as a function of frequency (Hz), phase (°) as a function of frequency, and specific reactance (Ohm-m) as a function of frequency. Idealized examples of these data plots are shown in FIG. 8, 9, and 10, respectively. Then, the following signal parameters are calculated based on the original or actual data and the modeled data. (In the following table "NN input" represents the corresponding parameter 1–20 that is entered into the neural network algorithm at the input and biased layers as shown in FIG. 15.)

DEFINITION OF PARAMETERS

| Abbreviation | Description | NN input | Measurement |
|---|---|---|---|
| $\|Z(\omega)\|$ | Frequency dependence of the impedance magnitude | | Directly measured data - impedance magnitude |
| PHASE(ω) | Frequency dependence of the phase of the impedance | | Directly measured data - impedance phase |
| RHO∞ | High frequency resistivity plateau | #3 | Assume a value, based on specific tissue biochemical properties (e.g. 1.1 Ω-m) |
| ALPHA | α Angle between the complex impedance locus center and low frequency real axis intercept. See FIG. 8. | #4 | Electrical behavior of ideal tissue can be mathematically modeled with: $Z_M(\omega) = R_\infty + (R_0 - R_\infty)/(1 + (j\omega\tau)^\alpha)$, where $Z_M$ is the modeled complex impedance, $\omega = 2\pi f$ is the measurement angular frequency (f is the frequency in Hz). Coefficients α, $R_\infty$, $R_0$ and $\tau = 1/\omega_{peak}$, are defined in FIG. 8. Also, $Z(\omega) = \|Z(\omega)\| (\cos \phi(\omega) + j \sin \phi(\omega)) = Re\{Z(\omega)\} + j\, Im\{Z(\omega)\}$ where φ is the impedance phase at a frequency. The coefficients are calculated numerically, based on the best fit semi-circle to the measured data in the frequency range from DC to approximately second measured point beyond $\omega_{peak}$ angular frequency (see FIG. 8). |
| TAU | $\tau = 1/\omega_{peak}$, inverse of the angular frequency that produces the highest reactive component of impedance | #5 | It is calculated numerically, in the same process as ALPHA. |

-continued

DEFINITION OF PARAMETERS

| Abbreviation | Description | NN input | Measurement |
|---|---|---|---|
| R0 | Low frequency resistance plateau | | Is calculated numerically, in the same process as ALPHA and TAU, see FIG. 8. |
| R∞ | High frequency resistance plateau | | Is calculated numerically, in the same process as ALPHA and TAU, see FIG. 8. |
| RHO0 | Low frequency resistivity plateau | #2 | Calculated as: RHO0 = RHO∞ · R0/R∞ |
| RHO(ω) | Frequency dependence of the resistivity (specific real component of the impedance). | | This function can be generated with the model, RHO(ω) = $Re\{Z_M(\omega)\}$ · RHO∞/$R_\infty$, or calculated from the measured impedance and phase: RHO(ω) = $Re\{Z(\omega)\}$ · RHO∞/$R_\infty$ = $\|Z(\omega)\|$ · COS(PHASE(ω)) · RHO∞/$R_\infty$ |
| IM(ω) measured | Frequency dependence of the specific reactance (specific imaginary component of the impedance) | | This function is calculated from the measured impedance and phase, and normalized with calculated values RHO∞ and $R_\infty$: IM(ω) = $Im\{Z(\omega)\}$ · RHO∞/$R_\infty$ = $\|Z(\omega)\|$ · SIN(PHASE(ω)) · RHO∞/$R_\infty$ |
| $IM_M(\omega)$ modeled | Frequency dependence of the specific reactance (specific imaginary component of the impedance) | | This function is generated with the model, and normalized with calculated values RHO∞ and $R_\infty$: $IM_M(\omega) = Im\{Z_M(\omega)\}$ · RHO∞/$R_\infty$ |
| $PHASE_M(\omega)$ modeled | Frequency dependence of the phase of the impedance | | This function is generated with a model, using the parameters calculated, as described for ALPHA. |
| REDS | Maximum slope of the resistivity dispersion for RHO(ω) | #6 | Found analytically for RHO(ω), based on the model parameters, explained for ALPHA. Can be calculated numerically, from data generated with the model (see ALPHA), using logarithmic frequency scale. |
| REDW | Width of the resistivity dispersion region for RHO(ω) | #7 | Found analytically for RH0(ω), based on the model parameters, explained for ALPHA. Defined as the width between the following two resistivity values: RHO0max = RHO0 − (RHO0 − RHO∞) · 10%, and RHO0min = RHO∞ + (RHO0 − RHO∞) · 10%. Can be calculated numerically, from data generated with the model, using logarithmic frequency scale. |
| FRECD | Central frequency for resistivity dispersion for RHO(ω) | #8 | Found analytically for RHO(ω), based on the model parameters, explained for ALPHA. This is a frequency for REDS. Can be calculated numerically, from data generated |

DEFINITION OF PARAMETERS

| Abbreviation | Description | NN input | Measurement |
|---|---|---|---|
| PHMAX | Maximum impedance phase angle for $PHASE_M(\omega)$ | #9 | with the model, using logarithmic frequency scale. Found analytically for $PHASE_M(\omega)$, based on the model parameters, explained for ALPHA. Can be calculated numerically, from data generated with the model, using logarithmic frequency scale. |
| FPHMAX | Frequency at which is PHMAX measured for $PHASE_M(\omega)$ | #10 | Found analytically for $PHASE_M(\omega)$, based on the model parameters, explained for ALPHA. Can be calculated numerically, from data generated with the model, using logarithmic frequency scale. |
| PHNS | Maximum negative slope of impedance phase for $PHASE_M(\omega)$ | #12, | Found analytically for $PHASE_M(\omega)$, based on the model parameters, explained for ALPHA. Can be calculated numerically, from data generated with the model, using logarithmic frequency scale. |
| PHNSW | Width of the negative slope of impedance phase for $PHASE_M(\omega)$ | #11 | Found analytically for $PHASE_M(\omega)$, based on the model parameters, explained for ALPHA. Defined as the width between the following two phase values: PHMAX · 10%, and PHMAX. Can be calculated numerically, from data generated with the model, using logarithmic frequency scale. |
| PHPS | Average positive slope of impedance phase for $PHASE(\omega)$ | #13 | Calculated numerically for $PHASE(\omega)$, for frequencies above FPHMAX on non-filtered measurement data. |
| PHPSW | Width of the positive slope of impedance phase for $PHASE(\omega)$ | | Calculated numerically for $PHASE(\omega)$, for frequencies above FPHMAX on non-filtered measurement data. Defined as the width between the following two phase values: PHMAX, and PHMAX · 30%. |
| PHSR | Ratio of PHPS and PHNS | #14 | Calculated, using already calculated parameters: PHSR = PHPS/PHNS |
| IMMAX | Maximum value of absolute specific reactance for $IM_M(\omega)$ | #15 | Found analytically for $IM_M(\omega)$, based on the model parameters, explained for ALPHA. Can be calculated numerically, from data generated with the model, using logarithmic frequency scale. |
| FIMMAX | Frequency at which IMMAX is measured for $IM_M(\omega)$ | #16) | Found analytically for $IM_M(\omega)$, based on the model parameters, explained for ALPHA. Can be calculated numerically, from data generated with the model, using logarithmic frequency scale. |
| IMNS | Maximum negative slope of specific reactance for $IM_M(\omega)$ | #18) | Found analytically for $IM_M(\omega)$, based on the model parameters, explained for ALPHA. Can be calculated numerically, from data generated with the model, using logarithmic frequency scale. |
| IMNSW | Width of the negative slope of specific reactance dispersion region for $IM_M(\omega)$ | #19 | Found analytically for $IM_M(\omega)$, based on the model parameters, explained for ALPHA. Defined as the width between the following two phase values: IMMAX · 10%, and IMMAX. Can be calculated numerically, from data generated with the model, using logarithmic frequency scale. |
| IMPS | Average positive slope of specific reactance dispersion region for $IM(\omega)$ | #17 | Calculated numerically for $IM(\omega)$, for frequencies above FIMMAX on non-filtered measurement data. |
| IMPSW | Width of the positive slope of specific reactance dispersion region for $IM(\omega)$ | | Calculated numerically for $IM(\omega)$, for frequencies above FIMMAX on non-filtered measurement data. Defined as the width between the following two phase values: IMMAX, and IMMAX · 30%. |
| IMSR | Ratio of IMPS and IMNS | #20 | Calculated, using already calculated parameters: IMSR = IMPS/IMNS |

Figure 11:
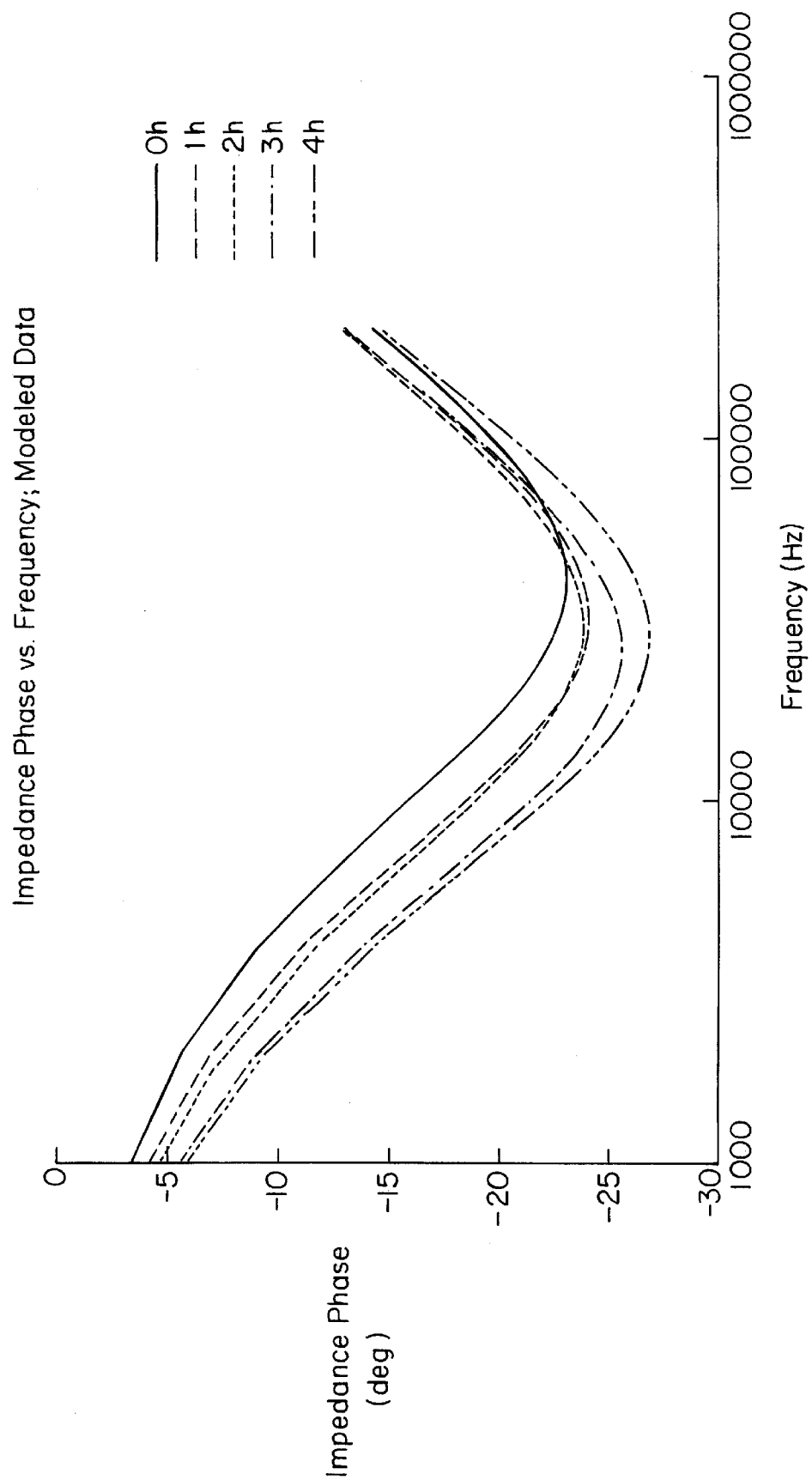
FIG. 11 is a plot of the tissue impedance phase as a function of frequency for the modeled data generated from the Cole-Cole plot.
Figure 12:
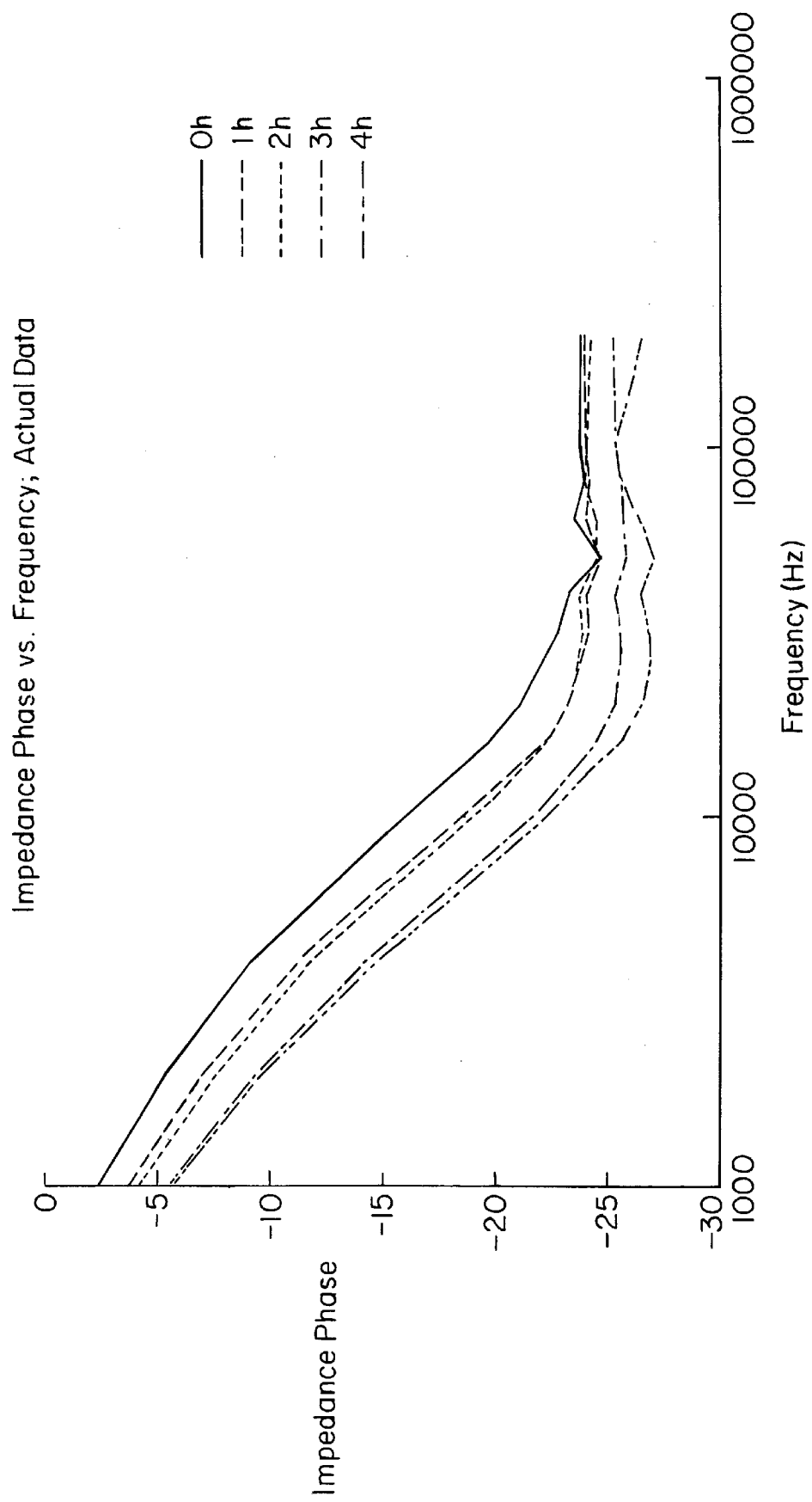
FIG. 12 is a plot of the tissue impedance phase as a function of frequency for the actual data detected from the spectral response of the tissue.
Figure 13:
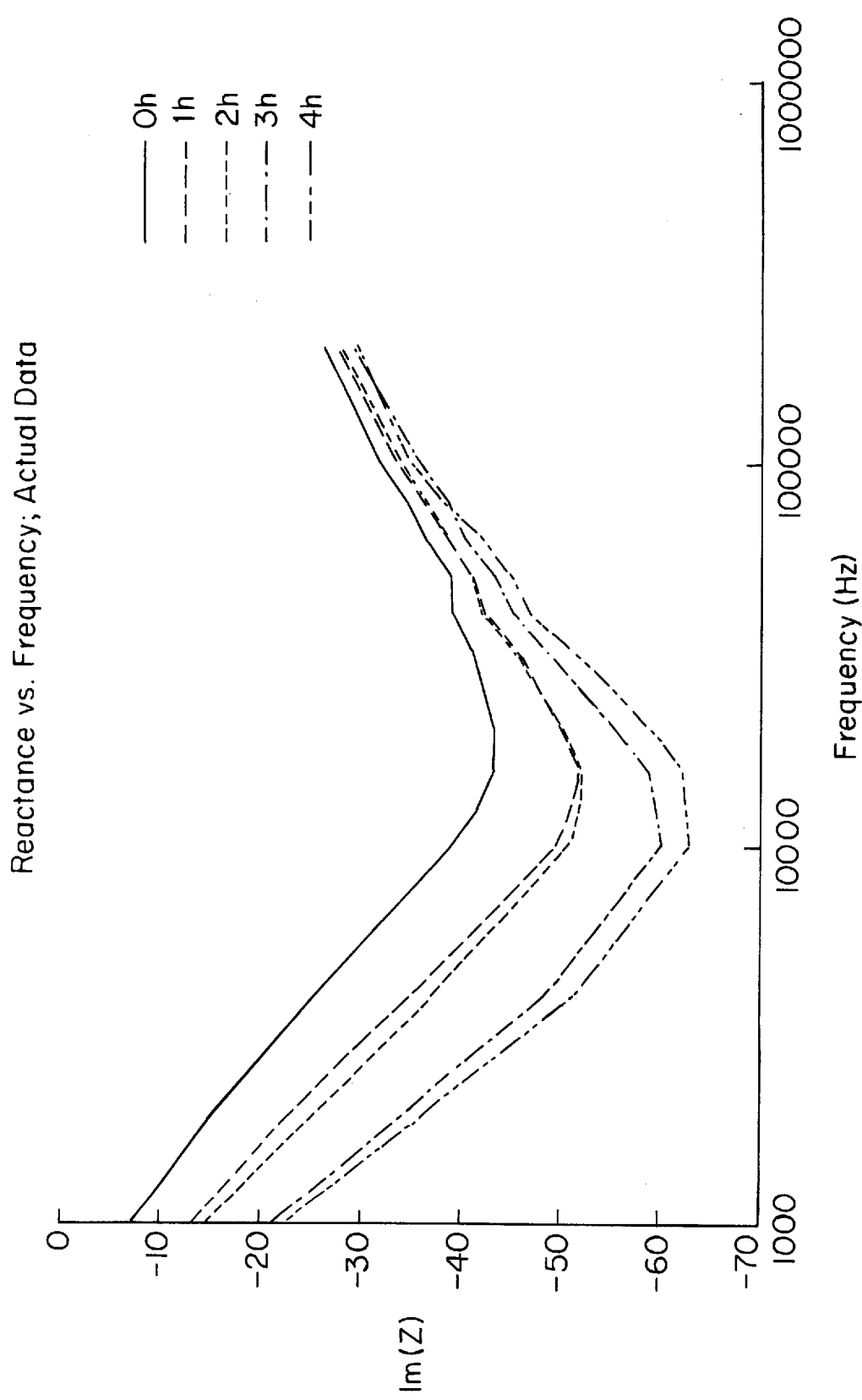
FIG. 13 is a plot of tissue reactance as a function of the frequency of the actual data detected from the spectral response of the tissue.
Figure 14:
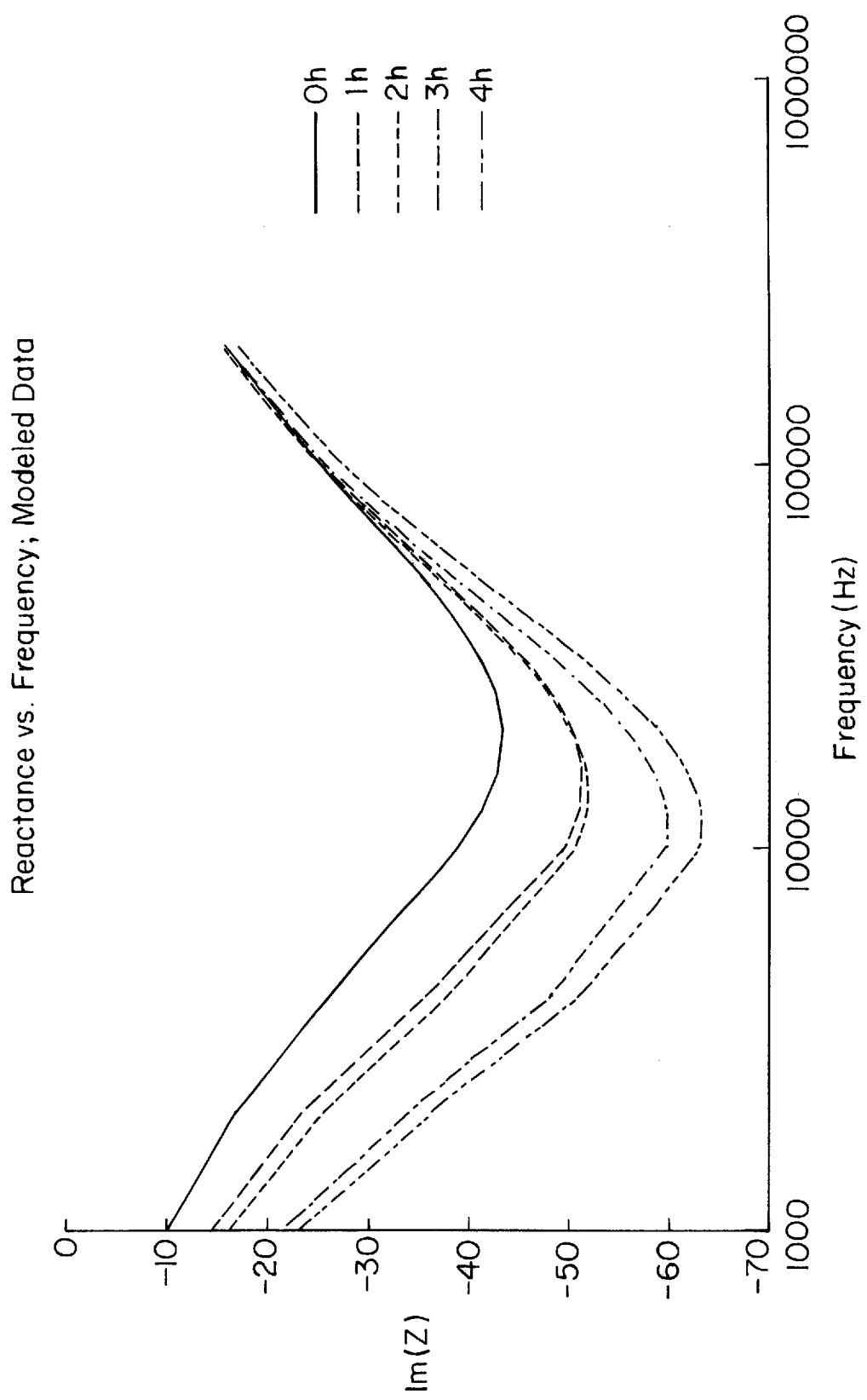
FIG. 14 is a plot of reactance as a function of frequency for the modeled data from the Cole-Cole plot.

Based upon the modeled and actual data, a number of different plots may be generated. FIG. 11, for example, shows the impedance phase as a function of frequency for the modeled data for a test subject at 0 hours through 4 hours after initiated ischemia. FIG. 12 is a plot of the impedance phase as a function of frequency for the actual data. FIG. 13 is the reactance as a function of frequency for the actual data. And finally, FIG. 14 is reactance as a function of frequency for the modeled data. From these plots, the set of parameters in the table is calculated for each of the modeled and actual data and then for each of the times at which data is captured.

Based on the low frequency amplitude plateaus RHO0, measured at the four electrode orientations, the longitudinal and transversal axes of the skeletal muscle being investigated are determined in step 525 relative to the electrodes. This is done using a pattern recognition scheme executed by the controller 310 aided by a numerical mathematical model that predicts the electric field and current distributions in an anisotropic (and inhomogeneous) medium of a known geometrical configuration, i.e., the electrode positions on the muscle. If the orientations of the electrodes are suboptimal as determined in step 530, the operator is instructed to rotate them to a position which provides for results of higher fidelity, see step 535. Operation then returns to the measuring impedance magnitude and phase in step 505.

If the electrodes are correctly placed, the series of parameters for both the original actual data and the modeled data may then be normalized based upon back-projection techniques for the resistive and capacitive components of the tissue being monitored in step 540. Specifically, back-projection techniques are used to calculate the capacitive and resistive components for the electrical model of the muscle, for example, illustrated in FIGS. 1 and 2. This is used to help normalize and preprocess the parameters calculated in step 520 prior to their insertion into the neural network algorithm.

In more detail, the system is based on the use of surface-spot (or needle) electrodes or coils, which generate an inhomogeneous electric current distribution in the tissue. Therefore, the measured resistance is a weighted line integral of the resistivities of individual resistive components. The weights and the values of the resistive components are calculated using an iterative-back-projection scheme in step 540 once an acceptable electrode orientation has been found. Four back-projections in step 540a (for four electrode orientations) are used to supply data to the previously mentioned model of the current distribution in the anisotropic tissue in step 540b. Due to its complexity, the numerical model can not be inverted. Therefore, it must be used as a direct model (based on the electrical and geometrical parameters to find the current distribution and resistance), and iterated, in order to find the best fit set of resistivities for tissue compartments, and their weights, according to the model in FIG. 2 that produce the measured values in step 540c.

Once the resistive weights and coefficients are determined, the same approach is used to estimate the capacitive weights and values in step 545. The difference is that these values are determined mostly using the phase and reactance related parameters such as the maximum phase angles, frequency of maximum angle, width of the phase angle dispersion, and slopes of the phase angle dispersion, and the descriptors of the resistivity behavior in the dispersion region such as the dispersion slopes, central dispersion frequency, and width of the dispersion region. Specifically, in step 545a four back-projections are again used to estimate the capacitive components. Then the estimated values are used to calculate total capacitances at the angles and frequencies in step 545b. The measured values and calculated values are compared in step 545c and iterated.

Data gained by the weights and values for the resistive and capacitive components based upon the back-projections is used to preprocess the parameters calculated in 520. This can be used to de-emphasize the contribution of any intervening layers of other muscle or fat. It can also be used to desensitize the system to any offset in electrode orientation relative to the underlying tissue. Specifically, by knowing the coefficients for cellular compartments, chemical structure of compartmental cellular fluids, occupancy ratios of the compartments, and cell membrane functionality, the tissue's physiological status can be described. This increases the accuracy of the system for ischemia measurements by adjustment of the parameters in step 550.

Finally, in step 555, the parameters are used as inputs for an artificial neural network algorithm. This neural network algorithm is previously trained when the system 300 is initially configured. It is trained to correlate the differences in the parameters to any one of a number of various characteristics. For example, the pattern matching scheme of the algorithm can use the parameters to generate an estimation of various tissue physiological characteristics such as: pH, absolute ischemia level, hypoxia level, tissue damage, tissue swelling, or cancer.

FIG. 15 shows one implementation of the three layered trained algorithm. It is realized as a one bias and nineteen input parameters. The weights given to each of these parameters are indicated by the size of the corresponding boxes (2–20). These parameters are used to calculate variables 21–26 at a hidden layer. The weights given to each of these hidden variables 21–26 is again indicated by the size of the associated boxes. The output layer 27 is then calculated from the hidden layer variables.

Those skilled in the art will recognize that different combinations of input parameters may be used. In order to assist in the convergence of the neural network, it is helpful to pick variables or parameters that are very predictive of the cell's abnormal state to be detected and of the normal level for the cell. As a result, it may be useful to combine parameters with each other in order to obtain better predictors for more accurate conversions. Similarly, those parameters which tend to not contribute to the output, represented by a small box for the input variables 2–20 at the input level, may be removed from the calculations.

Further, in other implementations, it may be helpful to increase the accuracy of the system by first running a test on a muscle that is known to be normal, i.e., not ischemic, for the particular patient. Data from this test run can be used to bias or preprocess the parameters prior to their input into the neural network.

The achieved result is "instantaneous"—it requires just a few sets of measurements, that can be performed in a short interval of time (less than a minute). The analysis does not require monitoring (numerous sets of measurements, performed in a long time period) to establish the reference base-line. It provides quantitative results.

Simple ischemia monitoring can be achieved by using a smaller number of measurement frequencies or with a single angular orientation of the electrodes.

When the above described system and method are applied to the detection of normal and pathological states, such as tumor cells, of tissue, the Cole-Cole plot in this application is again used to generate extrapolated data that is characteristic of the normal cells within the cell population for which the spectral response is obtained. This information, along with the actual spectral response, is used to generate the parameters for the pattern recognition algorithm. Of course, the algorithm must be properly trained for the desired search pattern for the abnormal tissue.

While this invention has been particularly shown and described with references to preferred embodiments thereof, it will be understood by those skilled in the art that various changes in form and detail may be made therein without departing from the spirit and scope of the invention as defined by the appended claims.

We claim:

1. A method for detecting ischemia in tissue, comprising:
   applying electrical energy to the tissue;
   detecting a spectral response of the tissue; and
   applying a transformation to the spectral response to determine a measure of ischemia of the tissue.

2. The method described in claim 1, wherein applying the transformation comprises:
   modeling the spectral response of the tissue when normal based upon the detected spectral response; and
   comparing the detected spectral response of the tissue and the modeled spectral response to determine the measure of the ischemia.

3. The method described in claim 2, wherein modeling the spectral response of the tissue when normal comprises extrapolating a resistance/reactance relationship at higher frequencies based upon a resistance/reactance relationship at lower frequencies of the detected spectral response.

4. The method described in claim 2, wherein modeling the spectral response of the tissue when normal comprises extrapolating a spectral response into higher frequencies based upon the detected spectral response at lower frequencies.

5. The method described in claim 4, wherein applying the transformation further comprises generating parameters that are descriptors of a spectral response of the ischemia of the tissue based upon the detected spectral response.

6. The method described in claim 5, wherein modeling the spectral response of the tissue when normal further comprises generating parameters that are descriptors of the spectral response of the tissue when normal based upon the extrapolated high frequency response.

7. The method described in claim 6, wherein comparing the detected spectral response of the tissue and the modeled spectral response comprises combining the parameters that are descriptors of the spectral response of the ischemia of the tissue and the parameters that are descriptors of the spectral response of the normal tissue in a pattern matching algorithm to generate a measure of the level of ischemia in the tissue.

8. The method described in claim 7, further comprising:
estimating resistive and/or capacitive components of an electrical model of the tissue; and
preprocessing the parameters prior to input into the pattern matching algorithm in response to the estimated components.

9. The method described in claim 8, wherein the resistive and capacitive components are estimated using a back-projection technique.

10. The method described in claim 8, wherein the estimated resistive components are used to determine volumes of compartments within the tissue.

11. The method described in claim 8, wherein the estimated resistive components are used to determine ionic concentrations of compartmental fluids in the tissue.

12. The method described in claim 8, wherein the estimated capacitive components are used to determine cell membrane functionality within the tissue.

13. The method described in claim 2, wherein applying the transformation further comprises normalizing the detected spectral response.

14. A method described in claim 13, wherein normalizing the detected spectral response comprises comparing resistance and reactive spectral responses with constraints based on known biochemical responses of tissues to obtain specific resistance and specific reactance frequency responses.

15. The method described in claim 1, wherein applying the transformation to the spectral response comprises combining parameters derived from the detected spectral response of the tissue in a pattern matching algorithm that is trained to generate a measure of the level of ischemia in the tissue from the parameters.

16. The method described in claim 1, wherein determining measures of ischemia comprises generating an estimated pH of the tissue.

17. A method for detecting a status of tissue, comprising:
applying electrical energy to the tissue;
detecting a spectral response of the tissue; and
combining parameters derived from the detected spectral response of the tissue in a pattern matching algorithm that is trained to generate a measure of the status of the tissue from the parameters.

18. The method described in claim 17, wherein the status of the tissue comprises whether or not the tissue contains abnormal cells.

19. The method described in claim 17, wherein the status of the tissue comprises whether or not the tissue contains tumor cells.

20. The method described in claim 17, wherein the status of the tissue comprises whether or not the tissue is hypoxic.

21. The method described in claim 17, wherein the status of the tissue comprises whether or not the tissue is damaged.

22. The method described in claim 17, wherein applying the transformation comprises:
modeling the spectral response of the tissue when normal based upon the detected spectral response; and
comparing the detected spectral response of the tissue and the modeled spectral response to determine the measure of the status.

23. The method described in claim 22, wherein modeling the spectral response of the tissue when normal comprises extrapolating a resistance/reactance relationship at higher frequencies based upon a resistance/reactance relationship at lower frequencies of the detected spectral response.

24. The method described in claim 22, wherein modeling the spectral response of the tissue when normal comprises extrapolating a spectral response into higher frequencies based upon the detected spectral response at lower frequencies.

25. A system for detection of tissue ischemia, the system comprising:
a synthesizer for generating electrical signals;
an electrical current source, responsive to the synthesizer, for generating electrical energy for transmission through tissue in response to the electrical signals;
means for applying the electrical energy from the current source to the tissue and for sensing voltages generated in the tissue in response to the electrical energy; and
a controller for determining measures of the ischemia in the tissue in response to detected spectral responses of the tissue based on the sensed voltages.

26. The system described in claim 25, wherein the controller models the spectral responses of the tissue when normal and compares the detected spectral responses of the tissue and the modeled spectral responses to determine the measures of the ischemia.

27. The system described in claim 26, wherein the controller models the spectral responses of the tissue when normal by extrapolating a spectral responses into higher frequencies based upon the detected spectral responses at lower frequencies.

28. The system described in claim 27, wherein the controller generates parameters that are descriptors of the spectral response of the ischemia of the tissue based upon the detected spectral responses.

29. The system described in claim 28, wherein the controller generates parameters that are descriptors of the spectral responses of the tissue when normal based upon the extrapolated high frequency response.

30. The system described in claim 29, wherein the controller executes a pattern matching algorithm that generates the measure of the ischemia by reference to the parameters that are descriptors of the spectral responses of the ischemia of the tissue and the parameters that are descriptors of spectral responses of the normal tissue.

31. A system for monitoring status of tissue comprising:

a synthesizer for generating electrical signals;

an electrical current source, responsive to the synthesizer, for generating electrical energy for transmission through tissue in response to the electrical signals;

means for applying the electrical energy from the current source to the tissue and for sensing voltages generated in the tissue in response to the electrical energy; and a controller that executes a pattern matching algorithm that is trained to generate a measure of the tissue's status in response to parameters derived from a spectral response of the tissue from the sensed voltages.

\* \* \* \* \*